United States Patent [19]

Cragoe, Jr. et al.

[11] 4,431,652

[45] Feb. 14, 1984

[54] 4-HYDROXY-5-SUBSTITUTED-3(2H)-ISO-THIAZOLONE-1,1-DIOXIDE DERIVATIVES USEFUL IN TREATING URINARY TRACT CALCIUM OXALATE LITHIASIS

[75] Inventors: Edward J. Cragoe, Jr., Lansdale; Clarence S. Rooney, Worcester, both of Pa.; Haydn W. R. Williams, Dollard des Ormeaux, Canada

[73] Assignees: Merck & Co., Inc.; Merck Sharp & Dohme (I.A.) Corp., both of Rahway, N.J.

[21] Appl. No.: 221,172

[22] Filed: Dec. 29, 1980

[51] Int. Cl.³ ............... A61K 31/44; C07D 275/02
[52] U.S. Cl. .................................. 424/270; 548/205; 548/206; 548/213; 548/214
[58] Field of Search ............... 548/205, 206, 213, 214; 424/270

[56] References Cited

U.S. PATENT DOCUMENTS 3,849,430 11/1974 Lewis ................................. 424/270
4,067,878 1/1978 Miller ................................ 424/270
4,346,094 8/1982 Beck et al. ........................ 548/206

OTHER PUBLICATIONS

Cottet et al., "Is There Treatment for Calcium Nephrolithiasis?", *Nouv. Presse Méd.* 5(3): 139–145 (1976).
Hautmann et al., "Calcium Oxylate . . . Disease . . . ", *J. of Urology*, pp. 712–715 (1978).
Randall et al., "Quantitative Structure . . . ," *J. Med. Chem.* 22:608 (1979).
Schwam et al., "Purification . . . Liver Glycolate . . . ", *Biochemistry* 13:2828–(1979).
Melon et al., "Experimental Oxalic Lithiasis . . . ," *Therapie XXVI* 991–998 (1971).
Thomas et al., "Traitement Hypooxalurigue . . . ," *Therapie XXVI* 999–1005 (1971).
Melon and Thomas, "Oxylate Nephrolithiasis . . . ", *Agressologie* 14(6): 357–365 (1973).
Thomas et al., "Succinate," *J. d'Urologie et Nephrologie* 80, No. 9 (1974).
Richardson, K. E., "Effect of Partial Hepatectomy . . . ", *Toxicology and Pharmacology* 24: 530–538 (1973).
J. Thomas, et al., "Recent Data on the Urinary Excretion . . . ", *Ann. Urol.* 6:(1): W 31–33 (1972).
Watts et al., ". . . Treatment . . . Hyperoxylurea . . . ," *Quarterly J. of Med., (New Series)* No. 190, pp. 259–272 (1978).

Scott et al, "Reduction in Urinary Oxylate . . . ", *Urology*, vol. 12: 212–214 (1978).
Smith, Lloyd, "Symposium on Stones," *Amer. J. Medicine*, pp. 649–653 (1968).
Williams, Hibbard et al., "Disorders of Oxylate Metabolism", *Amer. J. Medicine*, pp. 715–731 (1968).
Liao and Richardson, "Inhabition Oxalate Biosynthesis . . . ", *Archives Biochem. and Biophysics* 154: 68–75 (1972).
Liao and Richardson, "Metabolism Oxylate Precursers . . . ", *Archives Biochemistry and Biophysics* 153: 438–448 (1972).
Melon and Thomas, "Experimental Oxylate Lithiasis", *Therapie* 26: 985–990 (1971).
Lewis et al., *J. Het. Chem.*, p. 591 (1971).
Burger, *Medicinal Chemistry*, p. 42.
Randall et al., *J. Med. Chem.*, 22, p. 608.

*Primary Examiner*—Donald G. Daus
*Assistant Examiner*—G. Hendricks
*Attorney, Agent, or Firm*—Thomas E. Arther; Raymond M. Speer

[57] ABSTRACT

4-Hydroxy-5-substituted-3(2H)-isothiazolone-1,1-dioxide derivatives of the formula:

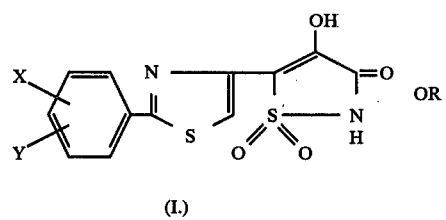

(I.)

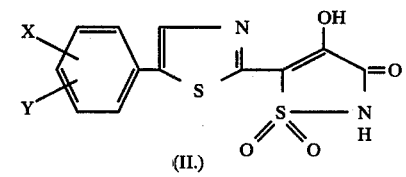

(II.)

where
X and Y are independently selected from the group consisting of hydrogen, halogen, and $C_{1-6}$ alkyl; provided that positions 2 and 6 of the substituted phenyl moiety may not be substituted by $C_{3-6}$ alkyl; or a pharmaceutically acceptable salt thereof;

useful in treating urinary tract, especially renal calcium oxalate lithiasis.

11 Claims, No Drawings

4-HYDROXY-5-SUBSTITUTED-3(2H)-ISOTHIAZOLONE-1,1-DIOXIDE DERIVATIVES USEFUL IN TREATING URINARY TRACT CALCIUM OXALATE LITHIASIS

BACKGROUND OF THE INVENTION

1. Field of the Invention

The present invention is concerned with novel 4-hydroxy-5-substituted-3(2H)-isothiazolone-1, 1-dioxide compounds useful in treating urinary tract, especially renal calcium oxalate lithiasis. The novel compounds of the present invention act as potent inhibitors of the enzyme glycolate oxidase.

The present invention is also concerned with a method of treating or preventing the formation of calcium oxalate urinary tract lithiasis, especially kidney or bladder stones, as well as pharmaceutical compositions useful in such a method, containing the novel 4-hydroxy-5-substituted-3(2H)-isothiazolone-1, 1-dioxide compounds as active ingredient.

Close to 70% of kidney stones are composed partially or predominantly of calcium oxalate; yet there is no satisfactory drug specific for the treatment of calcium oxalate urinary tract lithiasis, nor for prophylactic use by people prone to recurrent attacks of this disease.

Calcium oxalate lithiasis, the formation of stony concretions composed partially or predominantly of calcium oxalate, may occur at different points in the urinary tract, and is especially a problem in the kidney and in the bladder.

Approximately 70% of all renal calculi contain oxalate as the main anionic component of the matrix. In many, but not all patients, the condition is associated with a higher than normal level of metabolically produced oxalate.

Common procedures for treatment of renal lithiasis due to calcium oxalate consist of surgical removal of stones, or control of the diet to restrict intake of calcium and/or oxalate combined with ingestion of large quantities of water to dilute the urine. Attempts at chemotherapy have included the administration of magnesium oxide, orthophosphate, cellulose phosphate, isocarboxazide, thiazide diuretics, allopurinol and succinimide. Limited success has been realized so far by these drug approaches. No drug which specifically inhibits the biosynthetic formation of oxalic acid is available for the treatment of calcium oxalate urinary tract, especially renal lithiasis.

The major precursor of oxalate is glyoxylate. Thus, approaches to the reduction of the biosynthetic output of oxalic acid focus on (a.) the prevention of the conversion of glyoxylate to oxalate, and/or (b.) restriction of the production of glyoxylate from its precursors. A major pathway for the biosynthesis of oxalate can be represented as follows:

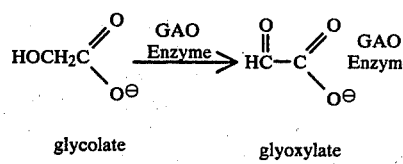

glycolate    glyoxylate

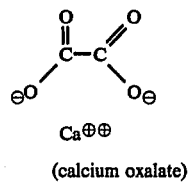

(calcium oxalate)

The same enzyme glycolate oxidase participates both in the biosynthesis of glyoxylate and, in its oxidation to oxalate. An inhibitor of the enzyme will act to block at two key points in the chain of reactions contributing to the production of oxalic acid. As a direct consequence of reducing oxalic acid levels in the urine with the compounds of this invention, the formation of oxalate calculi will be reduced or prevented in individuals whose urinary oxalate is primarily of metabolic origin.

The novel 4-hydroxy-5-substituted-3(2H)-isothiazolone-1,1-dioxide compounds described herein are potent inhibitors of glycolate oxidase and are thus useful in the treatment and prevention of urinary tract lithiasis, especially renal disease due to calcium oxalate stone formation in the kidney. As inhibitors of glycolate oxidase, the novel compounds of the present invention may also be useful in the treatment of primary hyperoxaluria. In the genetically inherited diseases designated hyperoxaluria types I and II, large quantities of oxalic acid are produced metabolically. Crystallization of calcium oxalate, occurring not only in the kidney and bladder, but in other tissues as well, frequently results in early death. The novel compounds of this invention may prove of value in the treatment of these rare but serious disease states.

2. Brief Description of the Prior Art

Glycolic acid oxidase inhibitors are described in U.S. Pat. Nos. 4,178,386; 4,207,329; and 4,233,452; as well as co-pending applications Ser. No. 074,465, filed Sept. 11, 1979, and Ser. No. 047,412, filed June 11, 1979. 5-Substituted-3(2H)-isothiazolone-1,1-dioxide compounds are described in Lewis et al., *J. Het. Chem.*, 8, p. 591 (1971). However, none of the compounds described in any of the above would suggest the novel 4-hydroxy-5-substituted-3(2H)-isothiazolone-1,1-dioxide compounds of the present invention.

SUMMARY OF THE INVENTION

The novel 4-hydroxy-5-substituted-3(2H)-isothiazolone-1,1-dioxide compounds of the present invention which are useful in treating and preventing urinary tract calcium oxalate lithiasis, especially the formation of calcium oxalate kidney or bladder stones, can be shown by the following formula:

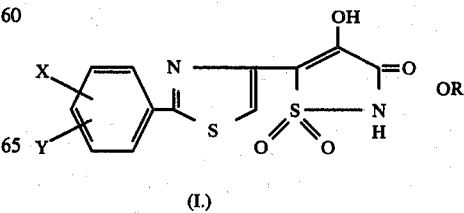

(I.)

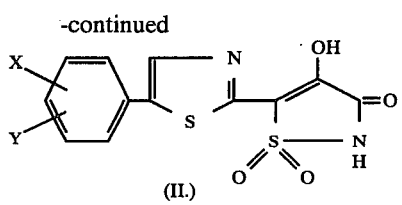

(II.)

where X and Y are independently selected from the group consisting of hydrogen, halogen, and $C_{1-6}$ alkyl; provided that positions 2 and 6 of the substituted phenyl moiety may not be substituted by $C_{3-6}$ alkyl; or a pharmaceutically acceptable salt thereof.

Also included within the scope of the present invention are the tautomeric forms of the compounds of Formula II, which may be shown by the following formula:

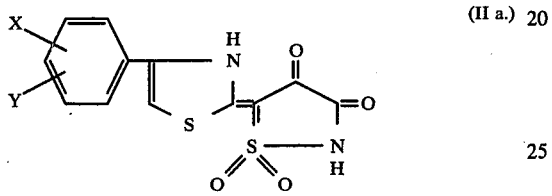

(II a.)

Particularly preferred compounds of Formulas I and II are the following:

5-[4-(3,4-dichlorophenyl)thiazol-2-yl]-4-hydroxy-3(2H)-isothiazolone-1,1-dioxide 5-[2-(3,4-dichlorophenyl)thiazol-4-yl]-4-hydroxy-3(2H)-isothiazolone-1,1-dioxide Included within the scope of the present invention are the pharmaceutically acceptable salts of the 4-hydroxy-5-substituted-3(2H)-isothiazolone-1,1-dioxide compounds.

Formula I and Formula II compounds are organic acids with a pKa in the range of 2 to 5 and thus can be used in the form of salts derived from inorganic or organic bases. Included among such salts are the following: metallic cations such as aluminum, calcium, lithium, magnesium, potassium, sodium, and zinc; and organic cations such as choline, diethanolammonium, n-methylglucammonium, ethanolammonium, diethylammonium, and triethanolammonium. Neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt. Water or oil-soluble or dispersible products are thereby obtained.

The Formula I and Formula II compounds can be administered to patients (both human and animal) having, or being prone, to calcium oxalate kidney or bladder stone disease by formulating them in a composition such as tablet, capsule or elixir for oral administration. Sterile solutions or suspensions can be used for parenteral administration. About 25 to 500 mg of a compound of Formula I or Formula II or a pharmaceutically acceptable salt is compounded with a pharmaceutically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose administered to patients having or prone to calcium oxalate kidney or bladder stone disease will be in the 50 mg to 2000 mg range with a preferred daily dose being 100 mg to 1000 mg of active ingredient. It will be realized by those skilled in the art that the dosage range for any particular patient (animal or human) will depend upon the severity of the disease treated, weight of the patient and any other condition which the physician or other person skilled in the art will take account of.

Illustrative of the adjuvants which may be incorporated in tablets, capsules and the like are the following: a binder such as gum tragacanth, acacia, corn starch or gelatin; an excipient such as dicalcium phosphate; a distintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup of elixir may contain the active compound, sucrose as a sweetening agent, methyl and propyl parabens as preservatives, a dye, and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The 4-hydroxy-5-substituted-3(2H)-isothiazolone-1,1-dioxide compounds of Formula I and Formula II may be prepared in accordance with a reaction scheme which may be illustrated as follows:

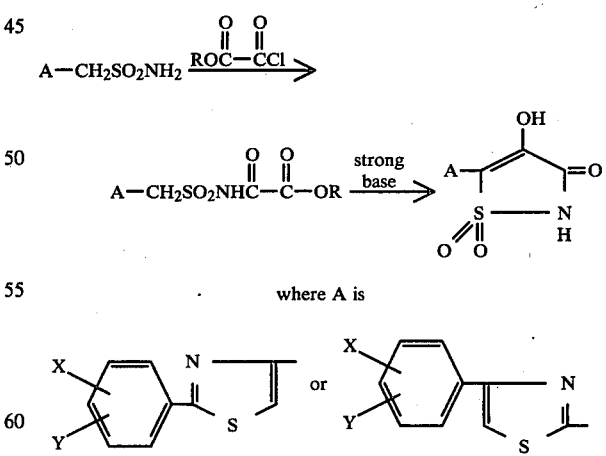

where A is and X and Y have the same meaning as above; and R is $C_{1-4}$ alkyl, preferably methyl or ethyl.

The first step of the reaction, in which the substituted benzylsulfonamide is reacted with $C_{1-4}$ alkyl oxalyl chloride, can be carried out neat in an excess of $C_{1-4}$ alkyl oxalyl chloride, with heating to about 100° C., followed by removal of the excess $C_{1-4}$ alkyl oxalyl chloride. Alternatively, an alkali metal salt of the benzylsulfonamide may be reacted with the $C_{1-4}$ alkyl oxalyl chloride in an aprotic solvent such as tetrahydrofuran or a mixture of tetrahydrofuran and toluene. Since the $C_{1-4}$ alkylmethanesulfonyloxamates which are produced are acidic, use of the alternative procedure requires acidification in order to obtain release of the desired product.

In the second step, reaction of the $C_{1-4}$ alkylmethanesulfonyloxamate intermediates in polar solvents such as dimethylformamide, tetrahydrofuran or ethanol, with a strong base such as potassium tert-butoxide, sodium ethoxide or the like, leads to intramolecular acylation and formation of the desired 4-hydroxy-5-substituted-3(2H)-isothiazolone-1,1-dioxide product as its salt. Acidification with mineral acid gives the desired product in its protonated form.

The [2-(substituted-phenyl) thiazol-4-yl]methanesulfonamide starting materials, i.e., where A in the reaction scheme illustrated above is:

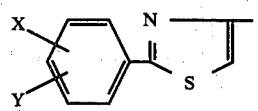

may be prepared as follows:

(1) a substituted thiobenzamide is treated with 1,3-dichloroacetone to give a 4-(chloromethyl)-2-(substituted-phenyl) thiazole;

(2) the 4-chloromethylthiazole is treated with thiourea to give the corresponding isothiouronium hydrochloride;

(3) the isothiouronium hydrochloride is treated with chlorine gas under acid conditions to give the corresponding sulfonyl chloride; and (4) the sulfonyl chloride is treated with concentrated ammonia to give the desired [2-(substituted-phenyl) thiazol-4-yl]methanesulfonamide starting material.

The above series of reactions may be illustrated by the following scheme

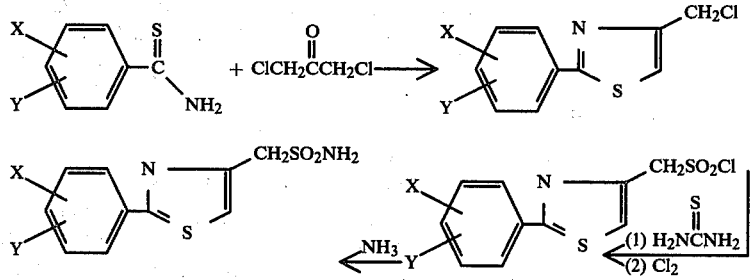

The [4-(substituted-phenyl)thiazol-2-yl]methanesulfonamide starting materials, i.e., where A in the reaction scheme illustrated above is:

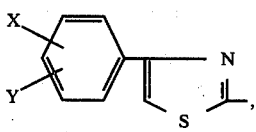

may be prepared as follows:

a substituted phenacyl halide is treated with sulfamoylthioacetamide at reflux to give the desired [4-(substituted-phenyl)thiazol-2-yl]methanesulfonamide starting material.

This reaction may be illustrated by the following scheme:

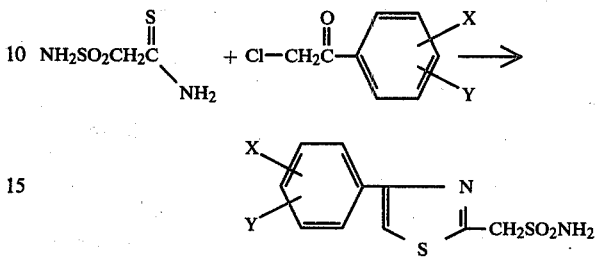

Following are examples which illustrate the preparation of representative compounds and compositions falling within the present invention, although no limitation is thereby intended.

EXAMPLE 1

5-[4-(3,4-Dichlorophenyl)thiazol-2-yl]-4hydroxy-3(2H)-isothiazolone-1,1-dioxide

Step A.
[4-(3,4-Dichlorophenyl)thiazol-2-yl]methanesulfonamide

A mixture of sulfamoylthioacetamide (7.7 g., 0.05 mol) and 3,4-dichlorophenacyl bromide (13.4 g., 0.05 mol) in ethanol (50 ml) was heated at reflux for 2 hours. After cooling and filtration there was obtained 11.5 g. of the desired intermediate, m.p. 187°–190° C.

Anal. Calc'd. for $C_{10}H_8Cl_2N_2O_2S_2$: % C, 37.16; % H, 2.49; % N, 8.67. Found: % C, 37.38; % H, 2.45; % N, 8.46.

Step B. Ethyl N-[[4-(3,4-dichlorophenyl)thiazol-2-yl]methanesulfonyl]-oxamate

To a solution of the (thiazol-2-yl) methanesulfonamide prepared in Step A above (3.2 g, 0.01 mol) in a mixture of tetrahydrofuran (25 ml) and toluene (15 ml) there was added a suspension of sodium hydride (50% in oil) 0.5 g, 0.01 mol) in toluene (15 ml). The mixture was heated at reflux for 15 minutes. While hot, there was added a solution of ethyloxalyl chloride (2.5 g, 0.02 mol) in toluene (10 ml). After heating on the steam bath for another 15 minutes, the mixture was cooled and then extracted twice with saturated sodium bicarbonate solution (150 ml). The aqueous phase was acidified with 6 N hydrochloric acid to give 3.1 g. of the substituted oxamate intermediate, m.p. 180°–182° C. Recrystallization from ethanol gave m.p. 182°–184° C.

Anal. Calc'd. for $C_{14}H_{12}Cl_2N_2O_5S_2$: % C, 39.72; % H, 2.86; % N, 6.62. Found: % C, 40.16; % H, 2.85; % N, 6.41.

Step C.
5-[4-(3,4-Dichlorophenyl)thiazol-2-yl]-4-hydroxy-3(2H)-isothiazolone-1,1-dioxide To a solution of the 2-thiazolylmethyl substituted oxamate intermediate prepared in Step B above (1.0 g., 0.0024 mol) in dimethylformamide (5 ml) was added potassium tert-butoxide (0.55 g, 0.0048 ml) in several portions over 15 minutes. The mixture was stirred at room temperature for 24 hours. After diluting with water (30 ml) and acidifying to congo red indicator paper, a yellow gum (1.1 g.) was obtained. Recrystallization was achieved by dissolving in boiling ether (500 ml), filtering, concentrating to a small volume, and adding petroleum ether. The yield of the title product was 0.3 g., m.p. 250° C. (dec.).

Anal. Calc'd. for $C_{12}H_6Cl_2N_2O_4S_2$: % C, 38.20; % H, 1.60; % N, 7.43. Found: % C, 38.36; % H, 1.63; % N, 7.32.

Following the procedures of Example 1, there may be prepared, for example, 5-[4-(3,4-dimethylphenyl)thiazol-2-yl]-4-hydroxy-3-(2H)-isothiazolone-1,1-dioxide, by substituting for the 3,4-dichlorophenacyl bromide in Step A, an equivalent amount of 3,4-dimethylphenacyl bromide. Similarly, other compounds of Formula II may be prepared following the procedures of Example 1, and substituting an equivalent amount of the appropriately substituted phenacyl halide.

EXAMPLE 2
5-[2-(3,4-Dichlorophenyl)thiazol-4-yl]-4-hydroxy-3(2H)-isothiazolone-1,1-dioxide

Step A.
4-(chloromethyl)-2-(3,4-dichlorophenyl)thiazole

A mixture of 3,4-dichlorothiobenzamide (8.24 g., 0.04 mol), 1,3-dichloroacetone (5.1 g., 0.04 mol) in acetone (150 ml) was stirred at room temperature overnight. After evaporation of the acetone under reduced pressure, the residue was dissolved in methanol (150 ml) and the solution refluxed 1½ hours. After cooling and removal of the methanol, the residue was slurried with a small quantity of methanol. The solids which formed after filtration showed m.p. 93°–96° C. (6.05 g.).

Anal. Calc'd. for $C_{10}H_6Cl_3NS$: % C, 43.11; % H, 2.17; % N, 5.03. Found: % C, 43.31; % H, 2.11; % N, 4.94.

Step B.
S-[2-(3,4-dichlorophenyl)thiazol-4-yl]methylisothiouronium hydrochloride A mixture of the 4-chloromethylthiazole intermediate prepared in Step A above (6.0 g., 0.021 mol), thiourea (2.0 g., 0.023 mol), and ethanol (50 ml) was heated under reflux for 3½ hours, and then allowed to stand at room temperature overnight. The ethanol was removed under vacuum. A small volume of acetone was added to the residue and the mixture filtered to give 4.2 g. of intermediate, m.p. 160°–165° C. Recrystallization from ethanol gave, m.p. 163°–170° C.

Anal. Calc'd. for $C_{10}H_6Cl_3NS$: % C, 37.25; % H, 2.84; % N, 11.85. Found: % C, 37.42; % H, 2.66; % N, 11.64.

Step C.
[2-(3,4-dichlorophenyl)thiazol-4-yl]methanesulfonyl chloride

Into a solution of the thiouronium salt intermediate prepared in Step B above (6.0 g., 0.017 mol) in glacial acetic acid (120 ml) was passed chlorine gas for 10 minutes at ice bath temperature. After stirring for another 10 minutes, the mixture was filtered to give 4.8 g. of crude product (after drying), m.p. 124°–127° C. Recrystallization from ether-petroleum ether gave m.p. 128°–130° C.

Anal. Calc'd. for $C_{10}H_6Cl_3NO_2S$: % C, 35.05; % H, 1.77; % N, 4.09. Found: % C, 35.03; % H, 1.82; % N, 3.86.

Step D.
[2-(3,4-Dichlorophenyl)thiazol-4-yl]methanesulfonamide

The sulfonyl chloride intermediate prepared in Step C above (15.3 g., 0.049 mol) was allowed to react with concentrated ammonia (150 ml) at room temperature for 10 minutes. On filtration there was obtained 8.75 g. of sulfonamide intermediate, m.p. 165°–167° C. Recrystallization from tetrahydrofuran-ether-petroleum ether gave m.p. 168°–170° C. Anal. Calc'd. for $C_{10}H_8Cl_2N_2O_2S_2$: % C, 37.16; % H, 2.49; % N, 8.67. Found: % C, 37.13; % H, 2.36; % N, 8.36.

Step E.
N-[[2-(3,4-dichlorophenyl)thiazol-4-yl]methanesulfonyl]oxamate

To a suspension of the thiazolyl-substituted methanesulfonamide derivative prepared in Step D above (6.5 g., 0.02 mol) in tetrahydrofuran (100 ml) and toluene (60 ml) was added sodium hydride (50% suspension in oil) (1.6 g., 0.034 mol). After stirring for 178 hour, there was added ethyl oxalyl chloride (4.0 g., 0.03 mol). The mixture was heated for 15 minutes on a steam bath. After cooling there was added ether (400 ml) and saturated sodium bicarbonate solution (200 ml). The white solid which formed was filtered. After washing with ether, the solids were suspended in water, and the mixture acidified with 6 N hydrochloric acid. Filtration gave 5.4 g. of the crude oxamate derivative. Recrystallization from ethanol gave 5.4 g., m.p. 153°–155° C.

Anal. Calc'd. for $C_{14}H_{12}Cl_2N_2O_5S_2$: % C, 39.72; % H, 2.86; % N, 6.62. Found: % C, 39.50; % H, 2.66; % N, 6.51.

Step F.
5-[2-(3,4-Dichlorophenyl)thiazol-4-yl]-4-hydroxy-3(2H)-isothiazolone-1,1-dioxide To a solution of the ethyl oxamate intermediate prepared in Step E above (4.4 g., 0.010 mol) in dimethylformamide (26 ml) was added potassium tert-butoxide (3.5 g., 0.032 mol) in portions over 15 minutes. After stirring overnight, the reaction mixture was poured into water (250 ml). Acidification with 6 N hydrochloric acid, followed by filtration, yielded 3.5 g. of crude product. Recrystallization from tetrahydrofuran-ether-petroleum ether gave 1.74 g. of the title compound, m.p. 301° C. (dec.).

Anal. Cald'd. for $C_{12}H_6Cl_2N_2O_4S_2$: % C, 38.20; % H, 1.60; % N, 7.42. Found: % C, 38.4; % H, 1.68; % N, 7.47.

Following the procedures of Example 2, there may be prepared, for example, 5-[2-(3,4-dimethylphenyl)- thiazol-4-yl]-4-hydroxy-3(2H)-isothiazolone-1,1-dioxide, by substituting for the 3,4-dichlorothiobenzamide in Step A, an equivalent amount of 3,4-dimethylthiobenzamide. Similarly, other compounds of Formula I may be prepared following the precedures of Example 2, and substituting an equivalent amount of the appropriately substituted thiobenzamide.

Example 3

Dry-filled Capsules Containing 50 mg. of Active Ingredient per Capsule

| Ingredient | Amount per Capsule |
|---|---|
| 5-[2-(3,4-dichlorophenyl)thiazol-4-yl-4-hydroxy-3(2H)-isothiazolone-1,1-dioxide | 50 mg. |
| Lactose | 149 mg. |
| Magnesium Stearate | 1 |
| Capsule (Size No. 1) | 200 mg. |

The active ingredient is reduced to a No. 60 powder and then the lactose and magnesium stearate are passed through a No. 60 bolting cloth onto the powder, and the combined ingredients are admixed for 10 minutes and then filled into a No. 1 dry gelatin capsule.

EXAMPLE 4

Glycolate Oxidase Enzyme Inhibition

The usefulness of the compounds of the present invention in treating urinary tract, especially renal, calcium oxalate lithiasis, was shown by the ability of these compounds to inhibit the glycolate oxidase enzyme. This inhibition was determined by observing the extent to which the test compound blocked the activity of the enzyme. The activity of the enzyme, in turn, was measured by following the rate of reduction of sodium 2,6-dichlorophenol-indophenol by sodium glycolate in the presence of the enzyme. The enzyme was pig liver glycolate oxidase. The reaction was following spectrophotometrically at 600 nm. The assay was conducted at 25° C. in a 0.10 M phosphate buffer, pH 7.0, continging 3 mM EDTA. Initial substrate concentrations were $5 \times 10^{-5}$ M of sodium 2,6-dichlorophenol-indophenol and $2 \times 10^{-4}$ M of sodium glycolate. Reactions were initiated by the addition of enzyme. Initial rates during the period from 1 to 3 min. after the addition of enzyme were recorded on a Beckman Acta M-VI spectrophotometer. One control was run simultaneously with three test reactions, and all initial rates were adjusted to a common control rate. For further details of this procedure, see Randall et al., *J. Med. Chem.*, 22, 6, 612 (1979).

The results obtained from this assay are illustrated below.

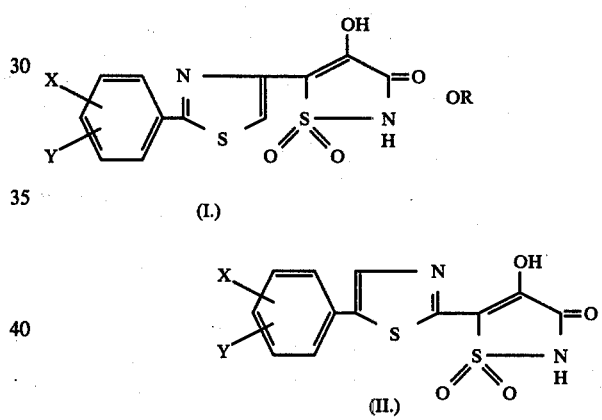

| Compound | IC$_{50}$ |
|---|---|
| 5-[4-(3,4-dichlorophenyl)thiazol-2-yl]-4-hydroxy-3(2H)-thiazolone-1,1-dioxide | $6 \times 10^{-7}$M |
| 5-[2-(3,4-dichlorophenyl)thiazol-4-yl]-4-hydroxy 3(2H)-isothiazolone-1,1-dioxide | $1.1 \times 10^{-7}$M |

The addition of other halogen and $C_{1-6}$ alkyl substituents to the phenyl moiety will serve to retain or improve the inhibitory activity of the 4-hydroxy-5-substituted-3(2H)-isothiazolone-1,1-dioxide compounds since lipophilicity is desired in the aromatic substituent.

What is claimed is:

1. A compound of the formula:

(I.)

OR (II.)

where
X and Y are independently selected from the group consisting of hydrogen, halogen, and $C_{1-6}$ alkyl, provided that positions 2 and 6 of the substituted phenyl moiety may not be substituted by $C_{3-6}$ alkyl;
or a pharmaceutically acceptable salt thereof.

2. A compound according to claim 1 wherein X and Y are both halogen.

3. A compound according to claim 2 wherein the compound is 5-[4-(3,4-dichlorophenyl)thiazol-2-yl]-4-hydroxy-3(2H)-isothiazolone-1,1-dioxide.

4. A compound according to claim 2 wherein the compound is 5-[2-(3,4-dichlorophenyl)thiazol-4-yl]-4-hydroxy-3(2H)-isothiazolone-1,1-dioxide.

5. A method of treating or preventing the formation of calcium oxalate urinary tract lithiasis, especially kidney or bladder stones, which comprises administering to a patient with, or prone to, such disease a therapeutically effective amount of a compound of the formula:

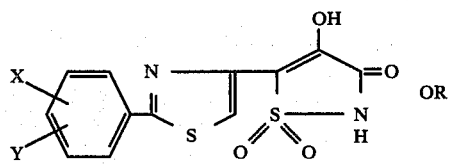

(I.)

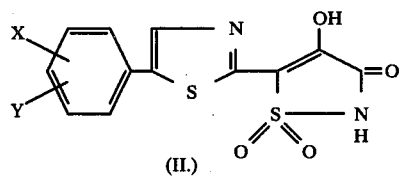

(II.)

where
X and Y are independently selected from the group consisting of hydrogen, halogen, and $C_{1-6}$ alkyl; provided that positions 2 and 6 of the substituted phenyl moiety may not be substituted by $C_{3-6}$ alkyl; or a pharmaceutically acceptable salt thereof.

6. A method according to claim 5 wherein the therapeutically effective amount is 50 mg. to 2000 mg. per day.

7. A method according to claim 5 wherein the compound administered is 5-[4-(3,4-dichlorophenyl)thiazol-2-yl]-4-hydroxy-3(2H)-isothiazolone-1,1-dioxide.

8. A method according to claim 5 wherein the compound administered is
5-[2-(3,4-dichlorophenyl)thiazol-4-yl]-4-hydroxy-3(2H)-isothiazolone-1,1-dioxide.

9. A pharmaceutical composition for use in treating or preventing the formation of calcium oxalate urinary tract lithiasis, especially kidney or bladder stones, comprising a pharmaceutically acceptable carrier and a compound of the formula:

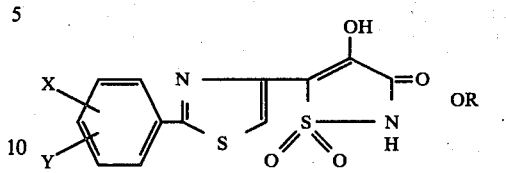

(I.)

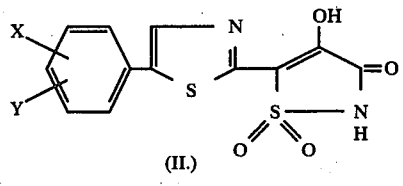

(II.)

where
X and Y are independently selected from the group consisting of hydrogen, halogen, and $C_{1-6}$ alkyl; provided that positions 2 and 6 of the substituted phenyl moiety may not be substituted by $C_{3-6}$ alkyl; or a pharmaceutically acceptable salt thereof.

10. A composition according to claim 9 wherein the compound is
5-[4-(3,4-dichlorophenyl)thiazol-2-yl]-4-hydroxy-3(2H)-isothiazolone-1,1-dioxide.

11. A composition according to claim 9 wherein the compound is 5-[2-(3,4-dichlorophenyl)thiazol-4-yl]-4-hydroxy-3(2H)-isothiazolone-1,1-dioxide.

* * * * *

UNITED STATES PATENT AND TRADEMARK OFFICE
CERTIFICATE OF CORRECTION

PATENT NO. : 4,431,652
DATED : February 14, 1984
INVENTOR(S) : EDWARD J. CRAGOE, JR., et al It is certified that error appears in the above-identified patent and that said Letters Patent is hereby corrected as shown below:

Column 5, lines 47-58 of structural formulas should read:

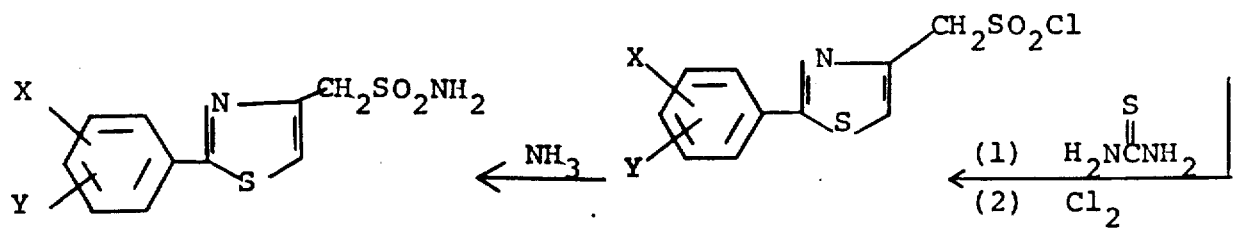

In Claim 1, Column 10, lines 38-43, structural formula II, should be corrected to read:

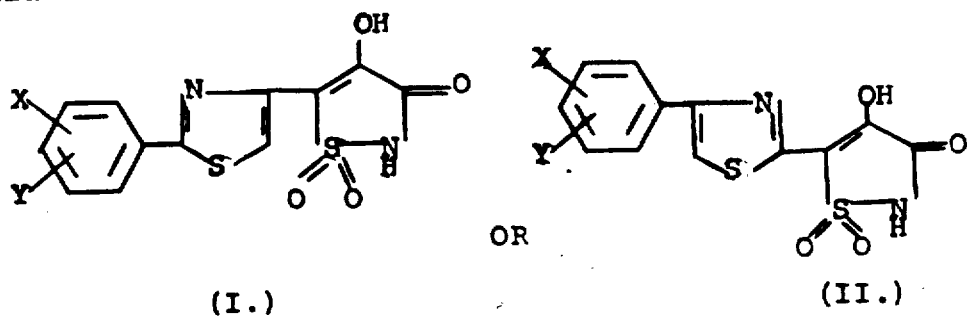

UNITED STATES PATENT AND TRADEMARK OFFICE
CERTIFICATE OF CORRECTION

PATENT NO. : 4,431,652

DATED : February 14, 1984

INVENTOR(S) : EDWARD J. CRAGOE, JR., et al

It is certified that error appears in the above-identified patent and that said Letters Patent is hereby corrected as shown below:

In Column 11, in Claim 5, lines 11-16, structural formula II should be corrected to read:

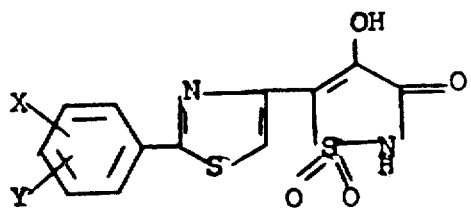     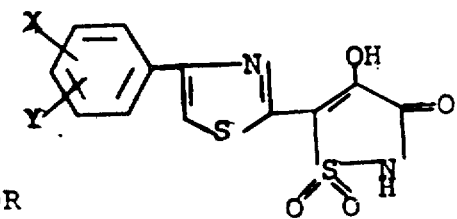

(I.)     OR     (II.)

UNITED STATES PATENT AND TRADEMARK OFFICE
CERTIFICATE OF CORRECTION

PATENT NO. : 4,431,652
DATED : February 14, 1984
INVENTOR(S) : EDWARD J. CRAGOE, JR., et al.

It is certified that error appears in the above—identified patent and that said Letters Patent is hereby corrected as shown below:

In Claim 9, column 12, lines 15-20, structural formula/should be corrected to read:

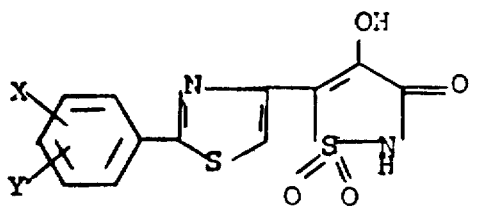

(I.)

OR

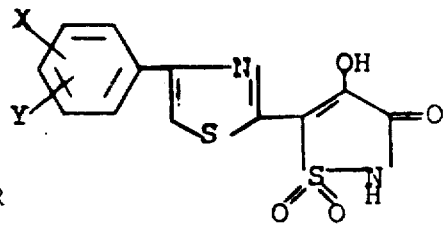

II (II.)

Signed and Sealed this

Tenth Day of July 1984

[SEAL]

Attest:

Attesting Officer

GERALD J. MOSSINGHOFF

Commissioner of Patents and Trademarks